US006365557B1

(12) United States Patent
Karol et al.

(10) Patent No.: US 6,365,557 B1
(45) Date of Patent: Apr. 2, 2002

(54) THIADIAZOLE ADDITIVES AND LUBRICATING COMPOSITIONS CONTAINING THE SAME

(75) Inventors: Thomas J. Karol, Norwalk; Ronald J. Tepper, Fairfield, both of CT (US)

(73) Assignee: R.T. Vanderbilt Company, Inc., Norwalk, CT (US)

( * ) Notice: Subject to any disclaimer, the term of this patent is extended or adjusted under 35 U.S.C. 154(b) by 0 days.

(21) Appl. No.: 09/693,138

(22) Filed: Oct. 20, 2000

Related U.S. Application Data

(60) Provisional application No. 60/160,568, filed on Oct. 20, 1999.

(51) Int. Cl.$^7$ .................. C10M 135/36; C07D 285/13; C07D 417/02
(52) U.S. Cl. ................ 508/274; 508/231; 548/142
(58) Field of Search .................... 548/142; 508/231, 508/274

(56) References Cited

U.S. PATENT DOCUMENTS

| | | | | |
|---|---|---|---|---|
| 3,161,575 A | | 12/1964 | Wells et al. ............ 204/52 |
| 4,136,043 A | | 1/1979 | Davis ................. 252/47.5 |
| 4,517,103 A | | 5/1985 | Hoffman ............... 252/28 |
| 4,908,144 A | | 3/1990 | Davis et al. ........... 252/47.5 |
| 5,026,865 A | * | 6/1991 | Karol ................. 548/142 |
| 5,055,584 A | | 10/1991 | Karol ................. 548/142 |
| 5,102,568 A | | 4/1992 | King et al. ........... 252/47.5 |
| 5,138,065 A | * | 8/1992 | Karol ................. 548/142 |
| 5,188,746 A | * | 2/1993 | Davis ................. 252/47.5 |
| 5,194,621 A | * | 3/1993 | Karol et al. ........... 548/142 |
| 5,318,712 A | | 6/1994 | Lange et al. .......... 252/47.5 |
| 5,512,190 A | | 4/1996 | Anderson et al. ....... 252/47 |
| 5,597,785 A | * | 1/1997 | Karol ................. 508/274 |
| 5,686,397 A | * | 11/1997 | Baranski et al. ....... 508/274 |
| 5,849,925 A | * | 12/1998 | Karol et al. .......... 548/142 |
| 6,150,307 A | * | 11/2000 | Camenzind et al. ..... 508/273 |

FOREIGN PATENT DOCUMENTS

| | | |
|---|---|---|
| EP | 0847998 | 6/1998 |
| JP | 09298107 | 5/1999 |

* cited by examiner

*Primary Examiner*—Ellen M. McAvoy
(74) *Attorney, Agent, or Firm*—Norris, McLaughlin & Marcus P.A.

(57) ABSTRACT

2,5-dimercapto-1,3,4-thiadiazole dimer-poly(ether)glycol reaction products and adducts useful as extreme pressure additives. Lubricating compositions (e.g., greases) containing reaction products and adducts exhibit improved Timken Load properties.

39 Claims, No Drawings

THIADIAZOLE ADDITIVES AND LUBRICATING COMPOSITIONS CONTAINING THE SAME

This application claims priority under 35 U.S.C. §119(e) from Provisional Application No. 60/160,568, filed Oct. 20, 1999.

FIELD OF THE INVENTION

The present invention relates to 2,5-dimercapto-1,3,4-thiadizaole dimer reaction products and adducts useful as extreme pressure additives, and more particularly to 2,5-dimercapto-1,3,4-thiadiazole dimer/glycol reaction products and adducts useful as extreme pressure additives.

BACKGROUND OF THE INVENTION

A variety of additives are used in lubricants to substantially improve performance. For example, extreme pressure additives are routinely incorporated into an untreated lubricating composition (e.g., greases) to significantly improve performance. Extreme pressure additives are believed to produce a film on the surface of a metal which can both increase the load carrying capacity of lubricant, and protects the metal surface under high load conditions from deterioration due to wear, welding, and abrasion.

Lead naphthenates and lead dialkyldithiocarbamates are frequently used as additives to improve the EP performance of greases. However, lead is a heavy metal which is considered "poisonous" in all forms. As an alternative, metal additives (such as antimony, zinc, and bismuth) have been used as a replacement for lead. However, these heavy metals still provide environmental concerns regarding the use. Accordingly, it has long been a goal in the art to develop non-metal lubricating materials to replace heavy metal additives while providing acceptable extreme pressure performance.

The effectiveness of potential extreme pressure additives is conventionally ascertained by the 4-Ball Weld Test (ASTM D-2596) and the Timken Load Test (ASTM D-2509). An ideal candidate compound should exhibit good results in both tests since each test quantitates different extreme pressure properties.

Known to those skilled in the art 2,5-dimercapto-1,3,4-thiadiazole (DMTD) derivatives are effective as anti-wear additives in lubricants. Examples of DMTD derivatives useful as anti-wear additives include the monosulfide and disulfide dimers of DMTD as disclosed in U.S. Pat. Nos. 4,517,103 and 5,194,621, maleate adducts of DMTD as disclosed in U.S. Pat. Nos. 5,102,568, 5,055,584 and 5,138,065 and mono-alkylated and thioacteal derivatives as disclosed in U.S. Pat. No. 5,849,925.

DMTD derivatives are also known to provide good 4-Ball Weld properties. In fact, the 4-Ball Weld properties of DMTD derivatives often exceed commercial requirements. Unfortunately, these same derivatives generally exhibit poor Timken Load performance since the DMTD derivatives do not generally provide Timken Loads levels greater than 35 pounds. As a result, commercialization of DMTD derivatives as extreme pressure additives has been limited.

In view of the above, there exists a need in the art for DMTD derivative that provide both adequate 4-Ball Weld and Timken Load properties. Accordingly, it is an object of the present invention to provide DMTD derivatives that provide adequate 4-Ball Weld and Timken Load properties, which will allow for the effective utilization of DMTD derivatives as extreme pressure additives.

SUMMARY OF THE INVENTION

The present invention provides 2,5-dimercapto-1,3,4-thiadiazole dimer/glycol reaction products and adducts useful as extreme pressure additives. In one embodiment, an additive is provided including the reaction product of:

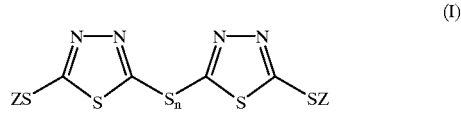

where Z is hydrogen, an alkyloxy linkage having formula (II):

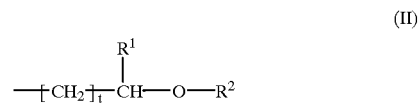

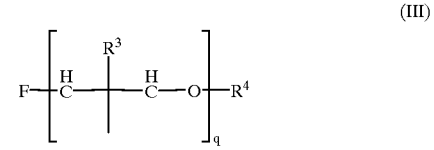

where F is a hydroxyl radical, a branched or straight chain $C_1$ to $C_{20}$ alkoxyl radical, a branched or straight chain $C_1$ to $C_{20}$ alkylcarboxyl radical, a mono-substituted, di-substituted, or tri-substituted glycerol residue, hydrogen, or combinations thereof; where $R^3$ is hydrogen, a methyl radical, or combinations thereof; where $R^4$ is hydrogen, a branched or straight chain $C_1$ to $C_{20}$ alkyl radical, a phenyl radical, a $C_1$ to $C_8$ branched or straight chain alkyl-substituted-phenyl radical, a $C_1$ to $C_{20}$ branched or straight chain acyl radical, or combinations thereof; and with q being 1 to 300.

In another embodiment, an additive is provided including mono-substituted and di-substituted thiadiazole condensation adducts having formulas (IV) and (V), respectively:

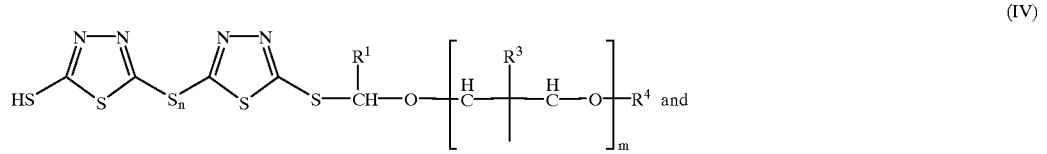

-continued

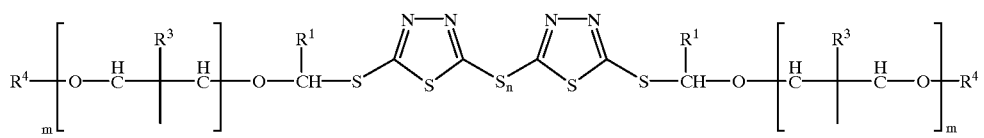
(V)

in which $R^1$, $R^3$ and $R^4$ are independently selected from the above-described group of substituents for the reaction products and n is 1 to 2. The number of repeating ether units "m" in the glycol moiety is 1 to 50.

In another embodiment, an additive is provided including the reaction product of: (A) a thiadiazole dimer having formula (VI):

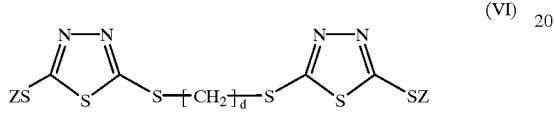
(VI)

where d is 1 to 5 and Z is hydrogen, an alkyloxy linkage having formula (II):

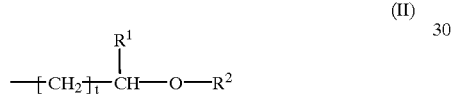
(II)

or combinations thereof, with $R^1$ being hydrogen, a branched or straight chain $C_1$ to $C_7$ alkyl radical, or combinations thereof and $R^2$ being hydrogen, a branched or straight chain $C_1$ to $C_7$ alkyl radical, or combinations thereof, wherein t is 0 or 1; and (B) a poly(ether)glycol having formula (III):

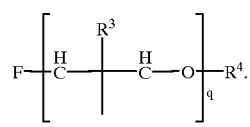
(III)

In an alternative embodiment, an additive is provided including the reaction product of:

(A) a thiadiazole compound being

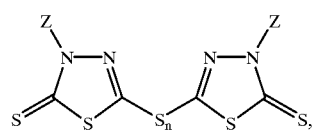
(IA)

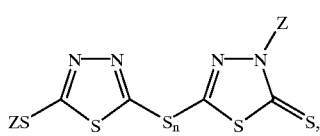
(IB)

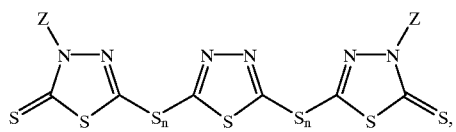
(IC)

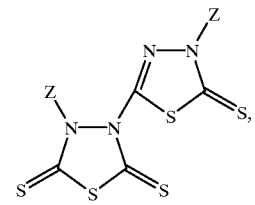
(ID)

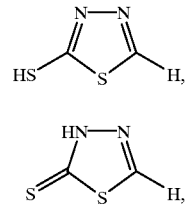
(IE)

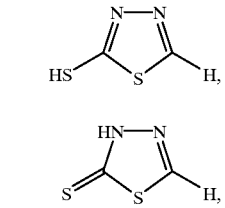
(IF)

or combinations thereof, where Z is hydrogen, an alkyloxy linkage having formula (II):

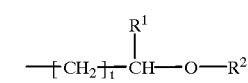
(II)

or combinations thereof, with $R^1$ being hydrogen, a branched or straight chain $C_1$ to $C_7$ alkyl radical, or combinations thereof and $R^2$ being hydrogen, a branched or straight chain $C_1$ to $C_7$ alkyl radical, or combinations thereof, where n is 1 to 2 and t is 0 or 1; and (B) a poly(ether)glycol having formula (III):

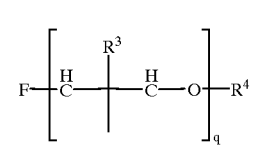
(III)

where F is a hydroxyl radical, a branched or straight chain $C_1$ to $C_{20}$ alkoxyl radical, a branched or straight chain $C_1$ to $C_{20}$ alkylcarboxyl radical, a mono-substituted, di-substituted, or tri-substituted glycerol residue, hydrogen, or combinations thereof; where $R^3$ is hydrogen, a methyl radical, or combinations thereof; where $R^4$ is hydrogen, a branched or straight chain $C_1$ to $C_{20}$ alkyl radical, a phenyl radical, a $C_1$ to $C_8$ branched or straight chain alkylsubstituted-phenyl radical, a $C_1$ to $C_{20}$ branched or straight chain acyl radical, or combinations thereof; and where q is 1 to 300.

Lubricating compositions including the reaction products and adducts of the present invention are also provided. Advantageously, the lubricating compositions of the present invention exhibit significantly improved Timken loads as compared previous DMTD derivatives. These and other advantages of the present invention will be readily apparent from the detailed description set forth below.

DETAILED DESCRIPTION OF THE INVENTION

Present invention provides reaction products and adducts of substituted-2,5-dimercapto-1,3,4-thiadiazole dimers (hereinafter "thiadiazole dimers") and poly(ether)glycols useful as extreme pressure additives in lubricants. The thiadiazole dimer-glycol reaction products and adducts have unexpectedly been found to provide good Timken Load properties in addition to good 4-Ball Weld properties. In addition, the reaction products and adducts are biodegradeble at low concentrations. Advantageously, the reaction products and adducts provide a more environmentally-friendly alternative to the heavy metal extreme pressure additives commonly used in lubricants.

In one embodiment the present invention provides an additive including a reaction product of a thiadiazole dimer and a poly(ether)glycol. The thiadiazole dimer is a 2,5-dimercapto-1,3,4-thiadiazole (DMTD) monsulfide or disulfide dimer having formula (I):

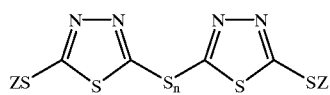

(I)

in which "n" is 1 to 2 and the substituent "Z" is either: (1) hydrogen; (2) an alkyloxy linkage having formula (II):

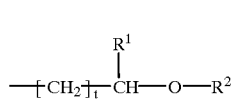

(II)

or combinations thereof. When Z is an alkyloxy linkage, "t" is 0 or 1 and the substituent $R^1$ is either: (1) hydrogen; (2) a branched or straight chain $C_1$ to $C_7$ alkyl radical, with a $C_1$ to $C_4$ alkyl radical being preferred; or a combination thereof. Likewise, the substituents for $R^2$ are independently chosen from the same group of substituents described for $R^1$. In a preferred embodiment, when Z is an alkyloxy linkage "t" is 0, $R_1$ is an ethyl radical and $R^2$ is a propyl radical.

Thiadiazole dimers falling within the above-described parameter are known in the art and are easily synthesized following known techniques. For example, the DMTD disulfide dimer (5,5'-dithiobis(1,3,4-thiadizole-2-thiol) is disclosed in U.S. Pat. Nos. 4,517,103 and 3,161,575, which are incorporated herein by reference. The DMTD disulfide dimer is also commercially available under the trade name VANLUBE®829 from R.T. Vanderbilt, Company, Inc. The DMTD monosulfide dimer (5,5'-thiobis (1,3,4-thiadiazole-2-thiol) is also commercially under the tradename VANAX®882A from R.T. Vanderbilt, Company, Inc. The thiadiazole dimers having the alkyloxy linkage of formula (II) with "t" being zero (0) are disclosed in U.S. Patent No. 5,194,621, which is incorporated herein by reference.

The second component for synthesizing the thiadiazole dimer-glycol reaction product is a poly(ether)glycol having formula (III):

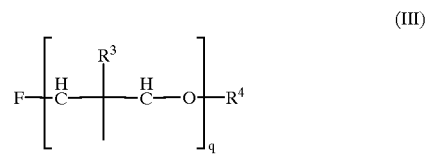

(III)

in which F is either: (1) a hydroxyl radical; (2) a branched or straight chain $C_1$ to $C_{20}$ alkoxyl radical, with a $C_1$ to $C_0$ radical being preferred; (3) a branched or straight chain $C_1$ to $C_{20}$ alkylcarboxyl radical, with a $C_1$ to $C_{10}$ radical being preferred; (4) a mono-substituted, di-substituted, or tri-substituted glycerol residue; (5) hydrogen; or a combination thereof. The substituent $R^3$ is either: hydrogen; a methyl radical; or a combination thereof The substituent $R^4$ is either: (1) hydrogen; (2) a branched or straight chain $C_1$ to $C_{20}$ alkyl radical, with a $C_1$ to $C_8$ radical being preferred; (3) a phenyl radical; (4) a branched or straight chain $C_1$ to $C_{20}$ alkyl-substituted-phenyl radical, with a $C_1$ to $C_8$ alkyl substituent being preferred; (5) a branched or straight chain $C_1$ to $C_{20}$ acyl radical, with a $C_1$ to $C_{10}$, radical being preferred; or a combination thereof. The number of ether repeating units "q" ranges from 1 to 300, with 1 to 150 being preferred, with 1 to 10 being more preferred.

Poly(ether)glycols falling within the above described parameters are known in the art. Representative examples of the glycols include, but are not limited to, polyethylene glycol, polypropylene glycol, tetraethylene glycol, ethyloxytriethylene glycol, butoxytriethylene glycol, dimethoxytriethylene glycol, triethyleneglycol di-nonanoate, butoxytriglycol, and triethyleneglycol dimethylether. One particularly preferred glycol is butoxytriethylene glycol. The glycols are commercial available from a variety of sources. Preferably, the glycols have a molecular weight from 340 to 4000, with 340 to 1000 being preferred. The glycols should have a viscosity less than 4000 centistokes at 25° C. for ease of handling. Likewise, the glycols should have a minimal effect on the dropping point of greases.

The reaction product is formed by combining the two sole components with or without a solvent and subsequently heating the components, if necessary. Preferably, the thiadiazole dimer is dispersed in the glycol, since the glycol is normally in a liquid state at room temperature. Heating the thiadiazole dimer-glycol reaction mixture is not required when the thiadiazole dimer is in a liquid state at room temperature. However, if the thiadiazole dimer is in a solid state at room temperature, the mixture may be heated (e.g., to at least 100° C.) to facilitate formation of the reaction product. The requisite temperature and time needed to facilitate formation of the reaction product is variable and can easily be determined by one skilled in the art. The formation of the liquid reaction product can approximated by observing the dissolution of the solid thiadiazole dimer. The formation of the reaction product can also be confirmed by Infrared Spectroscopy (IR) since shifts in absorption are observed when comparing the IR spectra for the individual components versus the IR spectra for the reaction product. In addition, to obtain a reaction product lighter in color, a small amount of a reducing agent (e.g., sodium meta bisulfite) is added to the reaction mixture.

The thiadiazole dimer and the poly(ether)glycol are preferably reacted in a molar ratio of the starting material of at least 0.2:1, with at least 0.4:1 being more preferred. However, for further improved extreme pressure properties an equimolar or excess of the thiadiazole starting material can be utilized (e.g., a molar ratio of 1:1, 2:1 or greater).

An alternative method for synthesizing the DMTD mono- and disulfide dimer-glycol reaction product is by reacting DMTD in the prescence of the glycol. It has been found that when DMTD is dispersed in the glycol and heated the DMTD mono- and disulfide dimer forms in situ, as well as 2-mercapto-1,3,4-thiadiazole (MTD). The in situ formation of the dimer can be discerned by the contemporaneous formation of hydrogen sulfide ($H_2S$). Accordingly, one skilled in the art would react 2 moles of DMTD for 1 mole of glycol to provide a DMTD dimer-glycol reaction product having a thiadiazole:glycol starting material ratio of 1:1.

While not wishing to be limited by theory, spectroscopic analysis of the above described reaction products indicate that various isomers of the thiadiazole dimer (I) and MTD monomer may be found in the reaction mixture. The presence of these other thiadiazole compounds is attributed to their presence in the thiadiazole starting material and to isomerization during formation of the reaction product. The thiadiazole compounds also complex with the above-described poly(ether)glycols to form reaction products useful as extreme pressure additives. Spectroscopic analysis indicates that the thiadiazole compounds have the following structures:

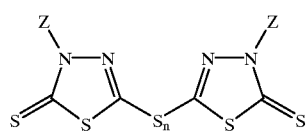
(IA)

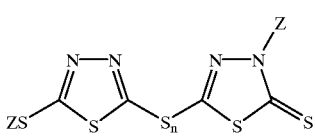
(IB)

-continued

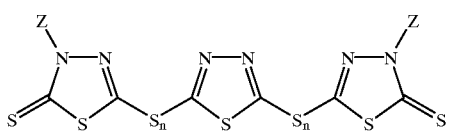
(IC)

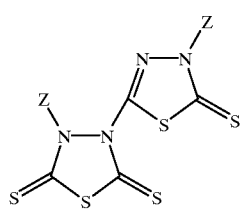
(ID)

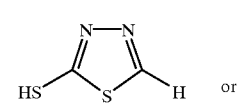
(IE)

or

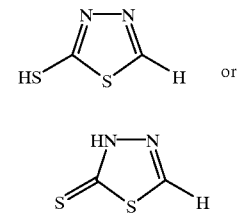
(IF)

Thus, in accordance with the present invention, the additives of the present invention can further include a mixture of reaction products. In a preferred embodiment, the additive contains the reaction product of the thiadiazole dinner having formula (I) with the poly(ether)glycols as the predominate reaction product, with the remainder being any of the reactions products formed by the thiadiazaole compounds of formulas (IA–IF) complexing with the poly(ether) glycols. The iw term "predominate" in this context preferably means at least 50 percent by weight of the total amount of reaction products present in the additive composition. In an alternative embodiment, the present invention provides an additive that includes at least one reaction product formed from any of the thiadiazole compound having formulas (IA) through (IF) and the above-described poly(ether)glycols.

In another embodiment the present invention provides an additive including mono-substituted and di-substituted thiadiazole condensation adducts having formulas (IV) and (V), respectively:

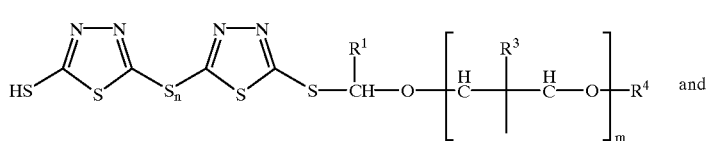
(IV)

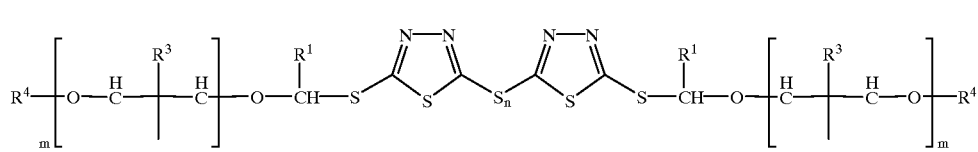
(V)

in which $R^1$, $R^3$ and $R^4$ are independently selected from the above-described group of substituents for the reaction products and n is 1 to 2. The number of repeating ether units "m" in the glycol moiety is 1 to 50, with 1 to 10 being preferred, and 1 to 3 being more preferred.

The substituted thiadiazole dimer-glycol adducts are prepared by reacting the DMTD monosulfide or disulfide dimer with an aldehyde containing the substituent $R^1$ and a poly (ether) glycol falling within the previously described parameters. The components are mixed and heated for a sufficient amount of time to form the condensation adduct. The synthesis of similar condensation adducts using monohydric alcohols instead of glycols are disclosed in U.S. Pat. No. 5,194,621, which is incorporated herein by reference. The mono-substituted thiadiazole dimer-glycol adduct is prepared by reacting the above-described components in a 1:1:1 molar ratio. The reaction mixture may also contain the di-substituted thiadiazole-glycol adduct if complete conversion of DMTD dimer does not occur. Incomplete conversion of DMTD dimer is ascertained by observing whether solid DMTD remains in the reaction mixture. As will be apparent to those skilled in the art, the di-substituted thiadiazole dimer-glycol adduct is prepared by reacting the components in a 1:2:2 molar ratio. Likewise, the reaction mixture may also contain mono-substituted thiadiazole dimer adduct. These parameters can be easily modified by one skilled in the art.

In yet another embodiment, the present invention provides an additive including a thiadiazole dimer- glycol reaction product having a DMTD dimer of formula (VI):

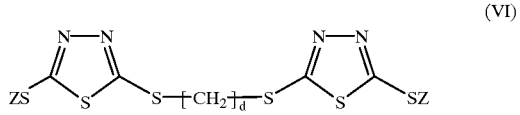

(VI)

where "d" is 1 to 5, with 1 to 3 being more preferred, and Z is hydrogen, an alkyloxy linkage having formula (II) as described above, or a combination thereof DMTD dimers having formula (VI) are easily synthesized using techniques known in the art. The poly(ether)glycol component and ratios of DMTD dimer to poly(ether)glycol are the same as described above. A particular advantage of the DMTD dimer of formula (VI) is increased oil-solubility due to the hydrocarbon bridge.

In accordance with present invention, the thiadiazole reaction products and adducts are incorporated as additives into lubricating compositions in an effective amount to impart adequate extreme pressure properties. In this context, adequate extreme pressure properties is passing a Timken Load of at least 40 pounds, with at least 50 pounds or greater being preferred. As will be apparent with one skilled in the art, the amount of the reaction products and adducts needed to provide adequate extreme pressure properties is variable. The additives can be added in a range from 0.1 to 10 weight percent of the lubricating composition, with at least 1 weight percent being preferred and 2 weight percent being even more preferred.

Lubricating compositions suitable for incorporation of the extreme pressure additives include, but are not limited to, lubricating oils, engine oils and lubricating greases containing a major amount of base oil. A "major amount" in this context means that greater than 50 weight percent (wt. %) of the composition is base oil. Base oils to be used include, but are not limited to, napthenic, aromatic, paraffinic, mineral, and synthetic oils. Representative synthetic oils include, but are not limited to, polysiloxanes, carboxylic acid esters and polyglycol ethers.

In a preferred embodiment, the lubricating composition is a grease which is prepared by adding to a base oil thickeners such as salts and complexes of fatty acid soaps, polyurea compounds, mixed and complex soaps of alkali metals, alkaline earth metals, aluminum, modified clays and quaternary ammonium bentonite complexes. Various other additives be incorporated as desired.

The following non-limiting examples illustrate the synthesis of the thiadiazole dimer-glycol reaction products and adducts, and their use as extreme pressure additives in lubricating compositions.

EXAMPLE 1

A thiadiazole dimer-glycol reaction product was synthesized by adding to a three-neck flask 112.9 grams of a DMTD disulfide dimer (5,5'-dithiobis(1,3,4-thiadizole-2-thiol) (i.e., formula (I) where Z is hydrogen ("H") and n is 2) and 138.6 grams of butoxytriethylene glycol to provide a 0.53:1 molar ratio of the starting material. The DMTD disulfide dimer is commercially available under the tradename VANLUBE®829 from R.T. Vanderbilt, Company, Inc. The mixture, which did not contain any other reactants, was heated from 1350° C. for 1 hour. After the mixture cooled, the unreacted solid material (i.e., the DMTD disulfide dimer) was removed from the liquid reaction product by filtration. The structure characteristics of this liquid reaction product (compound 1) is listed in Table 1.

EXAMPLES 2–4

Following the general procedure described in Example 1, thiadiazole dimer-glycol reaction products were prepared by mixing in a specified molar ratios the DMTD disulfide-dimer of Example 1 with poly(ether)glycols having the structure of formula (III). The substituent "Z" was either hydrogen or an alkyloxy linkage having the structure of formula (II). As in Example 1, the reaction mixtures were heated to at least 100° C. for at least 30 minutes. Once the mixtures cooled, the liquid reaction products were filtered to remove any unreacted thiadiazole dimer starting material. The structural characteristics of the reaction products (compounds 2–4) are listed in Table 1 below.

EXAMPLE 5

A thiadiazole dimer-glycol reaction product was synthesized using DMTD instead of a DMTD dimer. Approximately 16.3 grams of DMTD, 21.2 grams of triethylene glycol, and 0.14 grams of aluminum trichloride were added to a round bottom flask. The flask was attached to a scrubber containing sodium hydroxide to remove hydrogen sulfide during in situ dimer formation. The mixture was heated from 115–145° C. for 6 hours, in which $H_2S$ was observed to evolve indicating the in situ formation of the DMTD dimer. Once the reaction mixture was allowed to cool, the unreacted material was removed by filtering. The structural characteristics of the reaction product (compound 5) are listed in Table 1.

EXAMPLES 6–8

Thiadiazole dimer-glycol reaction products were prepared following the general procedure of Example 1 by mixing in specified mole ratios thiadiazole dimer having the structure of formula (I) with poly(ether)glycols having the structure of formula (III). The substituent "Z" was either hydrogen or an alkyloxy linkage having the structure of formula (II). As in Example 1, the mixtures were heated to at least 100° C. for at least 30 minutes. Once the mixtures cooled, the mixtures were filtered to remove any unreacted thiadiazole dimer starting material. The structural characteristics of the reaction products (compounds 6–8) are listed in Table 1.

EXAMPLE 9

A thiadiazole dimer-glycol reaction product was synthesized by converting DMTD in situ to DMTD dimer. Approximately 276.1 grams of DMTD and 367.2 grams of butoxytriethylene glycol were added to a three-neck flask. The flask was attached to a scrubber containing sodium hydroxide to remove hydrogen sulfide during in situ dimer formation. The mixture was bubbled with nitrogen and heated to 120° C. for approximately 5½ hours. After which, the flask was attached to an aspirator and heated for an additional hour. The reaction product was then filtered. The structural characteristics of the reaction product (compound 9) are listed in Table 1. Infrared analysis of the reaction product and its components was also performed with the following major peaks being identified:

| | |
|---|---|
| DMTD bis-dimer | 1487, 1435, 1406, 1262, 1212 $(cm^{-1})$; |
| Butoxytriethylene glycol | 1460, 1351, 1297, 1248 $(cm^{-1})$; |
| Compound 9 | 1510, 1433, 1350, 1244 $(cm^{-1})$. |

COMPARATIVE EXAMPLE 10–13

Comparative thiadiazole dimer-glycol reaction products were prepared following the general procedure of Examples 6–8. The structural characteristics of the reaction products (compound 10–13) are listed in Table 1.

TABLE 1

| Reaction Product | Z Type | n | Carbon Atoms | F | $R^3$ | q | $R^4$ | Thiadiazole: Glycol Ratio |
|---|---|---|---|---|---|---|---|---|
| Compound 1 | H | 2 | 0 | OH | H | 3 | Butyl | 0.53 |
| Compound 2 | H | 2 | 0 | OH | $CH_3$ | *(1) | OH | 5.2 |
| Compound 3 | H | 2 | 0 | OH | H | *(2) | OH | 1.0 |
| Compound 4 | H | 2 | 0 | OH | H | 4 | Butyl | 0.51 |
| Compound 5 | H | 1–2 | 0 | OH | H | 3 | OH | 0.37 |
| Compound 6 | H | 2 | 0 | OH | H, $CH_3$ | *(3) | OH | — |
| Compound 7 | H | 1 | 0 | OH | H | 3 | Butyl | 0.49 |
| Compound 8 | (II), t = 0 | 2 | 3 in $R^2$, 2 in $R^1$ | OH | H | 1 | Butyl | 1.0 |
| Compound 9 | H | 1–2 | 0 | OH | H | 3 | Butyl | 0.49 |
| Compound 10 | (II), t = 0 | 2 | 8 in R2, 7 in $R^1$ | OH | H | 1 | Butyl | 1.0 |
| Compound 11 | $CH_3$ | 2 | 0 | $CH_3$ | H | 3 | $CH_3$ | 0.41 |
| Compound 12 | (II), t = 0 | 2 | 8 in $R^2$, 7 in $R^1$ | OH | N/A | 0 | Butyl | 1.0 |
| Compound 13 | (II), t = 0 | 1 | 8 in $R^1$, $R^1$ = H | OH | H | 1 | Butyl | 1.0 |

(1)Commercially available polypropylene glycol sold under the trade name JEFFOX ®PPG2000 (m.w. ≈ 2000).
(2)Commercially available polyethylene glycol sold under the trade name CARBOWAX ®400 (m.w. ≈ 380–400).
(3)Commercially available poly(propy-,ethy-)lene glycol sold under the trade name ALKATERGE ®T-IV (m.w. - unknown).

EXAMPLE 14

A thiadiazole dimer-glycol adduct was synthesized by adding to a three-neck flask 135.9 grams of DMTD monosulfide dimer (5,5'-thiobis (1,3,4-thiadiazole-2-thiol), 16.0 grams of paraformaldehyde, and 100.1 grams of butoxytriethylene glycol to provide a 1:1:1 molar ratio of the starting material. The flask was attached to a Dean Stark apparatus and an aspirator. The mixture was heated for 1½ hours at 130° C. After the mixture cooled, the unreacted solid DMTD dimer was removed by a filtration. The structural characteristics of this liquid adduct (compound 14) is listed in Table 2. The reaction mixture is believed to contain both the mono-substituted and di-substituted DMTD dimer adducts since unreacted DMTD dimer remained in the flask.

EXAMPLES 15–19

Following the general procedure described in Example 14, thiadiazole dimer-glycol adducts were prepared by mix ing either the DMTD monosulfide or disulfide dimer, with an aldehyde containing the substituent $R^1$ and a poly(ether)glycol having the structure of formula (III) in approximately a 1:1:1 molar ratio. As in Example 14, the reaction mixtures containing the three reactants only were heated to at 100° C. for at least 30 minutes. Once the reaction mixtures cooled, the adducts were filtered to remove any unreacted DMTD dimer. The structural characteristics of the liquid adducts (compounds 15–19) are listed in Table 2. As in Example 14, the reaction mixtures are believed to contain both the mono-substituted and the di-substituted DMTD dimer adducts since unreacted DMTD dimer starting material remained in the flask.

TABLE 2

| Adduct | n | $R^1$ | $R^3$ | m | $R^4$ | Substitution |
|---|---|---|---|---|---|---|
| Compound 14 | 1 | H | H | 3 | Butyl | Mono & Bis |
| Compound 15 | 2 | H | H | 3 | Butyl | Mono & Bis |
| Compound 16 | 1 | H | $CH_3$ | 35[1] | Butyl | Mono & Bis |
| Compound 17 | 1 | H | $CH_3$ | 57[2] | Butyl | Mono & Bis |
| Compound 18 | 1 | 3-heptyl | H | 1 | Butyl | Mono & Bis |
| Compound 19 | 1 | H | H | 1 | Butyl | Mono & Bis |

[1]Average number for commercially available butoxypolypropylene glycol having an average molecular weight of 1550.
[2]Average number for commercially available butoxypolypropylene glycol having an average molecular weight of 1550.

EXAMPLE 20

A di-substituted thiadiazole dimer-glycol adduct was synthesized by adding to a three-neck flask 123.0 grams of DMTD monosulfide dimer, 28.8 grams of paraformaldehyde, and 181.2 grams of butoxytriethylene glycol to provide approximately a 1:2:2 molar ratio of the starting material. As in Example 14, the flask was attached to a Dean-Stark apparatus and an aspirator. The mixture was heated from 120–135° C. for approximately 4 hours. The structural characteristics of the liquid adduct (compound 20) are listed in Table 3.

EXAMPLES 21–22

Following the general procedure of Example 20, di-substituted thiadiazole-glycol adducts were prepared by mixing DMTD monosulfide dimer, an aldehyde containing the substituent $R^1$ and a poly(ether)glycol having the structure of formula (III) in approximately a 1:2:2 molar ratio of the starting materials. As in Example 20, the mixtures were heated to at least 100° C. for at least 30 minutes. The structural characteristics of the synthesized di-substituted adducts (compounds 21–22) are listed in Table 3.

TABLE 3

| Adduct | n | $R^1$ | $R^3$ | m | $R^4$ |
|---|---|---|---|---|---|
| Compound 20 | 1 | H | H | 3 | Butyl |
| Compound 21 | 1 | H | H | 3 | Butyl |
| Compound 22 | 1 | H | H | 1 | Butyl |

EXAMPLE 23

The reaction product of Example 1 (i.e., compound 1) was evaluated for its 4-Ball Weld and Timken Load properties in accordance with ASTM D-2596, and ASTM D-2509, respectively. Grease formulations were prepared using Lithium-12 hydroxystearate grease with various weight percents (wt. %) of compound 1 as an additive. As a comparison, grease formulations containing the DMTD disulfide dimer were also evaluated. The results are listed in Table 4.

TABLE 4

| Grease Sample | Compound 1 wt. % | DMTD Dimer wt. % | 4-Ball Weld (kgf) | Timken OK Load (pounds) |
|---|---|---|---|---|
| 1 | 10% | 0 | 620 | — |
| 2 | 5% | 0 | 620 | — |
| 3 | 3% | 0 | 400 | 80 |
| 4 | 2% | 0 | 400 | 80 |
| 5 | 1% | 0 | 315 | 80 |
| 6 | 0 | 4.5% | 800 | — |
| 7 | 0 | 3.0% | 620 | — |
| 8 | 0 | 2.0% | 500 | 20 |
| 9 | 0 | 1.0% | 315 | — |

As can be seen from Table 4, sample 8 (which contained 2.0 weight percent of the DMTD disulfide dimer) exhibited a commercially acceptable 4-Ball Weld of 500 kilograms force (kgf) with a commercially unacceptable Timken OK Load of 20 pounds. To the contrary, the sample 4 (which contained 2.0 wt. % of compound 1) exhibited a commercially acceptable 4-Ball Weld Load of 500 kgf with an outstanding Timken OK Load of 80 pounds. Thus, compound 1 provided a 400% increase in Timken Load performance over the DMTD disulfide dimer.

EXAMPLE 24

Lithium-12 hydroxystearate grease formulations were prepared containing varying weight percents of DMTD disulfide dimer and butoxytriethylene glycol to ascertain the individual 4-Ball Weld and Timken Load performances of the two reactants used to synthesize compound 1. The 4-Ball Weld and Timken Load tests were conducted using the same procedure used in Example 23. The results of the 4-Ball Weld and Timken Load tests are listed in Table 5 below.

TABLE 5

| Grease Sample | DMTD Dimer wt. % | Glycol wt. % | 4-Ball Weld (kgf) | Timken OK Load (pounds) |
|---|---|---|---|---|
| 1 | 0.90 | 1.10 | 315 | 30 |
| 2 | 0.45 | 0.55 | 250 | 30 |
| 3 | 0 | 2.0 | 160 | 10 |
| 4 | 2.0 | 0 | 500 | 20 |

Table 5 shows that grease formulations containing the individual components used to synthesize compound 1 do not exhibit commercially acceptable Timken Load properties. For example, sample 1 (which contained 0.90 wt. % DMTD disulfide dimer and 1.10 wt. % butoxytriethylene glycol for a total of 2.0 wt. % additive at thiadiazole:glycol molar ratio of 0.53) was only able to pass a Timken Load of 30 pounds. To the contrary, sample 4 of Table 4 (which contained 2 wt. % of compound 1 - the reaction product of DMTD disulfide dimer and butoxytriethylene glycol in a 0.53 molar ratio of starting materials) was able to pass a Timken Load of 80 pounds.

EXAMPLE 25

The reaction adducts, compounds 14 and 20, were evaluated for their Timken Load properties. Grease formulations were prepared from Lithium-12 hydroxystearate grease with approximately 2 wt. % of the adduct dispersed therein. Timken Load tests were conducted following ASTM D-2509 at 80 pounds to determine the compounds efficacy. The results are listed in Table 6.

TABLE 6

| Adduct | Timken OK Load (Pass or Fail) |
|---|---|
| Compound 14 | Pass - 80 lbs. |
| Compound 20 | Pass - 80 lbs. |

EXAMPLE 26

The reaction products, inventive compound 8 and comparative compounds 10–3, were evaluated for their Timken Load properties. Grease formulations were prepared from Lithium- 12 hydroxystearate grease with approximately 5 wt. % of the reaction product dispersed therein. Timken Load tests were conducted following ASTM-D-2509 at 50 pounds, and if warranted at 80 pounds, to determine efficacy. The results are listed in Table 7.

TABLE 7

| | Timken OK Load (Pass or Fail) | |
|---|---|---|
| Reaction Product | 50 lbs. | 80 lbs. |
| Compound 8 | Pass | Pass |
| Compound 10 | Fail | — |
| Compound 11 | Fail | — |
| Compound 12 | Fail | — |
| Compound 13 | Fail | — |

EXAMPLE 27

Various grease formulations were prepared containing 1 to 3 wt. % of compound 9, a DMTD mono- and disulfide dimer-butoxytriethylene glycol reaction product. Samples of the grease formulations were evaluated by the Timken Load test (ASTMD-2509), the 4-Ball Weld test (ASTMD-2596), and the 4-Ball Wear test (ASTMD-2266). The results are listed in Table 8.

TABLE 8

| Base Grease | Compound 9 (wt. %) | Timken OK Load (lbs.) | 4-Ball Weld (kgf) | 4-Ball Wear (mm) |
|---|---|---|---|---|
| Lithium-12 OH Stearate | 2.0 | 80 | 400 | 0.67 |
| | 1.5 | 70 | 315 | 0.59 |
| | 1.0 | 50 | 250 | 0.63 |
| Lithium Complex | 2.0 | 80 | 400 | 0.60 |
| | 1.5 | 60 | 315 | 0.64 |
| Aluminum Complex | 2.0 | 80 | 315 | 0.95 |
| | 1.5 | 50 | 250 | — |
| Polyurea | 3.0 | 40 | 250 | 0.84 |
| | 2.0 | 40 | 200 | 1.02 |
| Organo/Clay* | 3.0 | 60 | 250 | 0.64 |
| | 2.5 | Fail 60 | — | — |
| | 2.0 | 55 | 250 | 0.65 |

*Some softening of the grease was observed.

EXAMPLE 28

The biodegradibilty of compound 9 was evaluated following the "Proposed Standard Gledhill Shake Flask Test Method for Determining the Aerobic Aquatic Biodegradation of Lubricants and/or Their Components." This method is currently being considered by the ASTM and is known to those skilled in the art. The biodegradability assays were conducted using a commercially available apparatus. Compound 9 along with sodium benzoate (a positive control for water-soluble materials) and canola oil (a positive control for water-insoluble materials) were evaluated for 28 days using seed microorganisms sold under the trade name POLYSEED®, a product of Polybac Corporation. The biodegradability results are listed in Table 9.

TABLE 9

| Material | mg | % Degradation |
|---|---|---|
| Compound 9 | 18.2 | 78.0 |
| Compound 9 | 23.1 | 46.5 |
| Compound 9 | 52.9 | 8.4 |
| Sodium Benzoate | 36 | 78.4 |
| Canola Oil | 30.1 | 38.5 |

EXAMPLE 29

Compound 23 was prepared by converting substituent "Z" of the reaction product of Example 9 (i.e., compound 9) from hydrogen to 2-hydroxypropyl radical (i.e., formula (II) where $t=1, R_1$ is an ethyl radical and $R_2$ is hydrogen). Approximately 75 grams of the reaction product of Example 9 was placed in a three-neck flask and treated dropwise with excess propylene oxide (14.5 grams, 0.25 moles) for about two minutes. An exothermic reaction ensued and the temperature increased from 25° C. to 77° C. in about five minutes. The reaction mixture was then stirred for 15 minutes after which unreacted propylene oxide was removed by rotary evaporation.

EXAMPLE 30

Compound 24 was prepared by converting substituent "Z" of the reaction product of Example 9 (i.e., compound 9) was converted from hydrogen to a 2- hydroxybutyl radical (i.e., formula (II) where $t=1, R_1$ is a propyl radical and $R_2$ is hydrogen). Approximately 75 grams of the reaction product of Example 9 was placed in a three-neck flask and treated dropwise with excess 1,2-epoxybutane (18.0 grams, 0.25 moles) for about one minute. An exothermic reaction ensued and the temperature increased from 27° C. to 73° C. in about five minutes. The reaction mixture was then stirred for 1 hour after which unreacted 1,2-epoxybutane was removed by rotary evaporation.

EXAMPLE 31

A thiadiazole dimer-glycol reaction product (compound 25) was prepared having a DMTD dimer of formula (VI) with "d" being 2 and Z being hydrogen. The dimer was first prepared by adding to a three-neck flask 330.8 grams of a solution of the DMTD sodium half salt (33% active, 0.634 moles) and 100 mL of isopropanol. 44.0 grams of 1,2 dichloroethane (0.445 moles) was then slowly added to the mixture. An additional 133.6 grams of the DMTD half salt solution was added (for a total of 464.4 grams, 0.890 moles). The reaction mixture was heated to 80° C. and stirred for approximately three hours. The reaction mixture exhibited a significant amount of white solid precipitate. Approximately 110 mL of solvent was removed by distillation. The white solid was collected, washed with water and dried in an oven at 58° C.

The reaction product was prepared by adding 59.5 grams of the white solid and 72.7 grams of butoxytriethylene glycol to a three neck flask. The reaction mixture was heated to 128° C. for one hour after which an additional 16.7 grams of butoxytriethylene glycol. The mixture was heated for an additional two hours. The liquid product was filtered to remove unreacted solids. The liquid product was titrated with 0.1 M KOH, which indicated that the liquid product was 29% active. The reaction product had a thiadiazole:glycol molar ratio of approximately 0.26:1.

EXAMPLE 32

Compound 25 and its DMTD dimer component were evaluated for their Timken Load properties. Grease formulations were prepared from Lithium-12 hydroxystearate grease with approximately 5 wt. % of the additive dispersed therein. Timken Load tests were conducted following ASTM-D-2509 at 50 pounds, and if warranted at 80 pounds, to determine efficacy. The results are listed in Table 10.

TABLE 10

|  | Timken OK Load (Pass or Fail) | |
| --- | --- | --- |
| Reaction Product | 50 lbs. | 80 lbs. |
| Compound 25 | Pass | Pass |
| DMTD dimer (VI) | Fail | — |

We claim:

1. An additive for use in lubricants comprising a reaction product of:

(A) a thiadiazole dimer having formula (I):

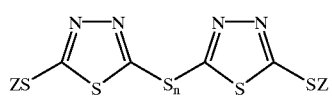

where Z is selected from the group consisting of hydrogen, an alkyloxy linkage having formula (II):

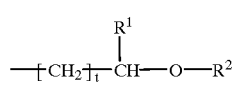

and combinations thereof, with $R^1$ being selected from the group consisting of hydrogen, a branched or straight chain $C_1$ to $C_7$ alkyl radical, and combinations thereof and $R^2$ being selected from the group consisting of hydrogen, a branched or straight chain $C_1$ to $C_7$ alkyl radical, and combinations thereof, wherein n is 1 to 2 and t is 0 or 1; and (B) a poly(ether)glycol having formula (III):

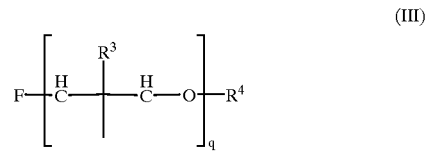

where F is selected from the group consisting of a hydroxyl radical, a branched or straight chain $C_1$ to $C_{20}$ alkoxyl radical, a branched or straight chain $C_1$ to $C_{20}$ alkylcarboxyl radical, a mono-substituted, di-substituted, or tri-substituted glycerol residue, hydrogen, and combinations thereof; where $R^3$ is selected from the group consisting of hydrogen, a methyl radical, and combinations thereof; where $R^4$ is selected from the group consisting of hydrogen, a branched or straight chain $C_1$ to $C_{20}$ alkyl radical, a phenyl radical, a $C_1$ to C8 branched or straight chain alkyl-substituted-phenyl radical, a $C_1$ to $C_{20}$ branched or straight chain acyl radical, and combinations thereof; and wherein q is 1 to 300.

2. The additive of claim 1, wherein Z is hydrogen.

3. The additive of claim 1, wherein Z is the alkyloxy linkage where $R^1$ and $R^2$ are independently $C_1$ to $C_4$ alkyl radicals and t is 0.

4. The additive of claim 1, wherein F is a hydroxyl radical.

5. The additive of claim 1, wherein F is a $C_1$ to $C_{10}$ alkylcarboxyl radical.

6. The additive of claim 1, wherein $R^3$ is hydrogen.

7. The additive of claim 1, wherein $R^4$ is a $C_1$ to $C_8$ alkyl radical.

8. The additive of claim 1, wherein $R^4$ is a $C_1$ to $C_{10}$ acyl radical.

9. The additive of claim 7, wherein $R^4$ is a butyl radical.

10. The additive of claim 1, wherein the thiadiazole dimer and poly(ether)glycol are reacted in a ratio of at least 0.2:1.

11. The additive of claim 1, wherein the thiadiazole dimer and poly(ether)glycol are reacted in a ratio of at least 0.4:1.

12. The additive of claim 1, wherein q is from 1 to 150.

13. The additive of claim 1, wherein q is from 1 to 10.

14. An additive for use in lubricants, comprising a thiadiazole-glycol adduct selected from the group consisting of a mono-substituted adduct having formula (IV):

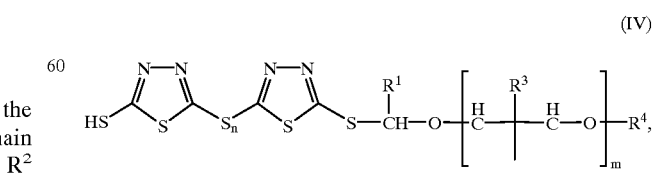

a di-substituted adduct having formula (V):

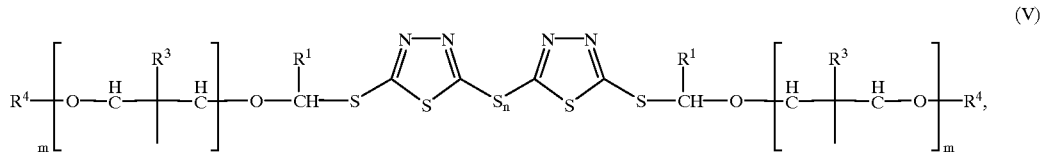

and combinations thereof, where $R^1$ is selected from the group consisting of hydrogen, a branched or straight chain $C_1$ to $C_7$ alkyl radical, and combinations thereof; where $R^3$ is selected from the group consisting of hydrogen, a methyl radical, a hydroxyl radical, and combinations thereof; where $R^4$ is selected from the group consisting of a hydrogen, a $C_1$ to $C_{20}$ branched or straight chain alkyl radical, a phenyl radical, a branched or straight chain $C_1$ to $C_{20}$ alkyl-substituted-phenyl radical, a branched or straight chain $C_1$ to $C_{20}$ acyl radical, and combinations thereof; and wherein n is from 1 to 2 and m is from 1 to 50.

15. The additive of claim 14, wherein $R^1$ is a $C_1$ to $C_4$ alkyl radical.

16. The additive of claim 14, wherein $R^1$ is hydrogen.

17. The additive of claim 14, wherein $R^4$ is hydrogen.

18. The additive of claim 14, wherein $R^4$ is a $C_1$ to $C_8$ alkyl radical.

19. The additive of claim 18, wherein $R^4$ is a butyl radical.

20. The additive of claim 14, wherein m is 1 to 10.

21. A lubricating composition comprising a major amount of a base oil and an effective amount of the additive of claim 1.

22. The lubricating composition of claim 21, wherein the additive is at least 2 weight percent of the composition.

23. A lubricating composition comprising a major amount of a base oil and an effective amount of the additive of claim 14.

24. The lubricating composition of claim 23, wherein the additive is at least 2 weight percent of the composition.

25. An additive for use in lubricants comprising a reaction product of:

(A) a thiadiazole dimer having formula (VI):

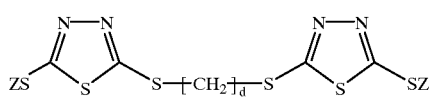

where d is 1 to 5 and Z is selected from the group consisting of hydrogen, an alkyloxy linkage having formula (II):

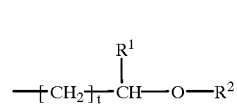

and combinations thereof, with $R^1$ being selected from the group consisting of hydrogen, a branched or straight chain $C_1$ to $C_7$ alkyl radical, and combinations thereof and $R^2$ being selected from the group consisting of hydrogen, a branched or straight chain $C_1$ to $C_7$ alkyl radical, and combinations thereof, wherein t is 0 or 1; and (B) a poly(ether)glycol having formula (III):

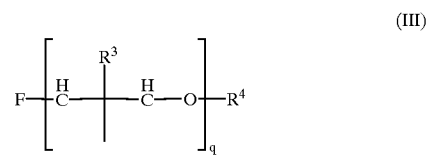

where F is selected from the group consisting of a hydroxyl radical, a branched or straight chain $C_1$ to $C_{20}$ alkoxyl radical, a branched or straight chain $C_1$ to $C_{20}$ alkylcarboxyl radical, a mono-substituted, di-substituted, or tri-substituted glycerol residue, hydrogen, and combinations thereof; where $R^3$ is selected from the group consisting of hydrogen, a methyl radical, and combinations thereof; where $R^4$ is selected from the group consisting of hydrogen, a branched or straight chain $C_1$ to $C_{20}$ alkyl radical, a phenyl radical, a $C_1$ to $C_8$ branched or straight chain alkyl-substituted-phenyl radical, a $C_1$ to C20 branched or straight chain acyl radical, and combinations thereof; and wherein q is 1 to 300.

26. The additive of claim 25, wherein d is 1 to 3.

27. The additive of claim 25, wherein Z is hydrogen.

28. The additive of claim 25, wherein F is a hydroxyl radical.

29. The additive of claim 25, wherein F is a $C_1$ to $C_{10}$ alkylcarboxyl radical.

30. The additive of claim 25, wherein $R^3$ is hydrogen.

31. The additive of claim 25, wherein $R^4$ is a $C_1$ to $C_8$ alkyl radical.

32. The additive of claim 25, wherein $R^4$ is a $C_1$ to $C_{10}$ acyl radical.

33. The additive of claim 31, wherein $R^4$ is a butyl radical.

34. The additive of claim 25, wherein the thiadiazole dimer and poly(ether)glycol are reacted in a ratio of at least 0.2:1.

35. The additive of claim 34, wherein the thiadiazole dimer and poly(ether)glycol are reacted in a ratio of at least 0.4:1.

36. The additive of claim 25, wherein q is from 1 to 150.

37. The additive of claim 36, wherein q is from 1 to 10.

38. A lubricating composition comprising a major amount of a base oil and an effective amount of the additive of claim 25.

39. An additive for use in lubricants comprising a reaction product of:

(A) a thiadiazole compound selected from the group consisting of

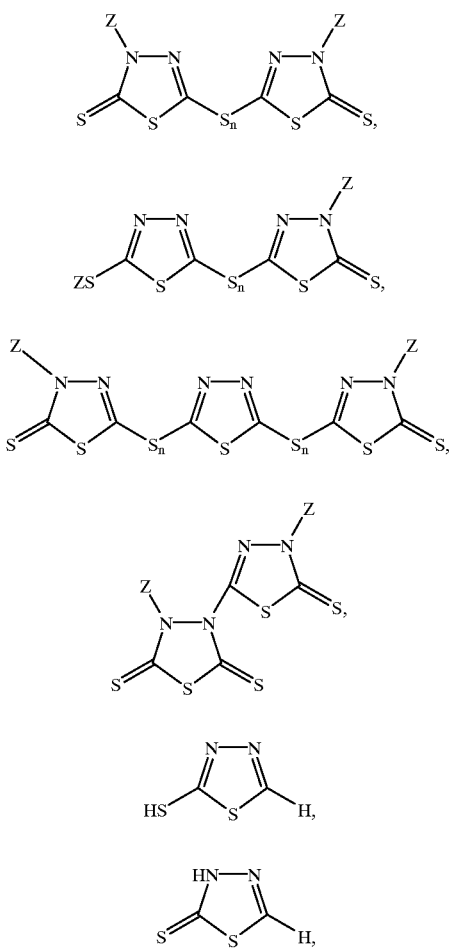

(IA)
(IB)
(IC)
(ID)
(IE)
(IF)

and combinations thereof, where Z is selected from the group consisting of hydrogen, an alkyloxy linkage having formula (II):

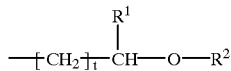

(II)

and combinations thereof with $R^1$ being selected from the group consisting of hydrogen, a branched or straight chain $C_1$ to $C_7$ alkyl radical, and combinations thereof and $R^2$ being selected from the group consisting of hydrogen, a branched or straight chain $C_1$ to $C_7$ alkyl radical, and combinations thereof, wherein n is 1 to 2 and t is 0 or 1; and (B) a poly(ether)glycol having formula (III):

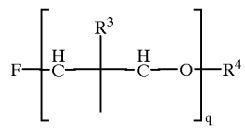

(III)

where F is selected from the group consisting of a hydroxyl radical, a branched or straight chain $C_1$ to $C_{20}$ alkoxyl radical, a branched or straight chain $C_1$ to $C_{20}$ alkylcarboxyl radical, a mono-substituted, di-substituted, or tri-substituted glycerol residue, hydrogen, and combinations thereof; where $R^3$ is selected from the group consisting of hydrogen, a methyl radical, and combinations thereof, where $R^4$ is selected from the group consisting of hydrogen, a branched or straight chain $C_1$ to $C_{20}$ alkyl radical, a phenyl radical, a $C_1$ to $C_8$ branched or straight chain alkyl-substituted-phenyl radical, a $C_1$ to $C_{20}$ branched or straight chain acyl radical, and combinations thereof; and wherein q is 1 to 300.

* * * * *